(12) United States Patent
Sochor

(10) Patent No.: US 7,794,256 B1
(45) Date of Patent: Sep. 14, 2010

(54) IMPLANTABLE CONNECTOR WITH CONTACT-CONTAINING FEEDTHROUGH PINS

(76) Inventor: Jerzy Roman Sochor, 425 Costa Mesa Ter., Apt. D, Sunnyvale, CA (US) 94085

(*) Notice: Subject to any disclaimer, the term of this patent is extended or adjusted under 35 U.S.C. 154(b) by 173 days.

(21) Appl. No.: 12/187,392

(22) Filed: Aug. 7, 2008

Related U.S. Application Data

(60) Provisional application No. 60/954,954, filed on Aug. 9, 2007.

(51) Int. Cl.
  *H01R 13/28* (2006.01)
(52) U.S. Cl. .............................. 439/289; 439/909
(58) Field of Classification Search ............ 439/73, 439/270, 289, 521, 668, 669, 909
  See application file for complete search history.

(56) References Cited

U.S. PATENT DOCUMENTS

| | | | | |
|---|---|---|---|---|
| 4,715,380 A | * | 12/1987 | Harris | ............................ 607/37 |
| 4,904,213 A | * | 2/1990 | Hock et al. | .................. 439/824 |
| 6,321,126 B1 | * | 11/2001 | Kuzma | ......................... 607/137 |
| 6,415,168 B1 | | 7/2002 | Putz | |
| 6,662,035 B2 | * | 12/2003 | Sochor | ......................... 600/378 |
| 7,195,523 B2 | | 3/2007 | Naviaux | |
| 7,534,127 B2 | * | 5/2009 | Parker et al. | ................. 439/425 |
| 7,553,193 B2 | | 6/2009 | Kast et al. | |

\* cited by examiner

*Primary Examiner*—Tho D Ta
*Assistant Examiner*—Travis Chambers

(57) ABSTRACT

An implantable connector electrically connects multi-conductor leads to an implantable medical device such as a neurostimulator. The connector is assembled directly into a hermetic feedthrough of the device and utilizes the feedthrough housing as a sustaining structure for connector pressurization. The feedthrough pins are adapted to directly connect, confine, protect, and precisely position respective resilient compressible contacts. The compressible contacts can be coil springs, metal-particle-filled elastomer buttons, and fuzz buttons, and can be used with rigid tips where a contact preload and/or an enhanced contact tip robustness is desired. In one method of connector assembly an iso-diametric lead proximal terminal is first inserted into a seal without significant interference, and the resulting lead-seal assembly is subsequently installed in a clamping cover. Connector pressurization means include space-efficient latching clips which support contact forces and the seal compression by engaging undercuts on the feedthrough housing side walls.

33 Claims, 11 Drawing Sheets

IMPLANTABLE CONNECTOR WITH CONTACT-CONTAINING FEEDTHROUGH PINS

CROSS-REFERENCE TO RELATED APPLICATIONS

This application claims priority of provisional patent application Ser. No. 60/954,954, filed 2007 Aug. 9 by the present inventor.

FEDERALLY SPONSORED RESEARCH

Not Applicable

SEQUENCE LISTING OR PROGRAM

Not Applicable

BACKGROUND

1. Field

This relates to implantable medical devices having external electrical connections and electrical feedthroughs, specifically to miniature implantable connectors for interconnection of implantable devices and associated lead wires.

2. Prior Art

In a typical implantable electronic device, such as a cochlear implant, heart pacemaker, or a brain-stimulating device, the device contains electronic circuitry (electronics) that resides in a hermetic housing or case. The device is attached to at least one electrical lead ("lead") that has sensing and/or stimulating electrodes on its end distal from the device which are implanted in the tissue targeted for therapy (cochlea, heart muscle, particular area of brain, etc.). Other leads may connect the device to additional implantable system components, such as drug delivery devices, implantable inductive coils (for energy delivery to the device and/or data communication with the device), or power sources, which may have to reside in a more accessible body area for easier charging and/or replacement.

It is preferable that the implantable leads and devices be detachable so that either a device or leads can be implanted or explanted independently. This functionality is provided by a connector on the device's case, which disengageably connects the proximal (near-device) lead terminals to the device's electronics. The connector's contacts must connect with the device's electronics across a hermetic feedthrough so that the hermeticity of the device's case is not compromised, i.e., the electronics remains sealed from the body fluids and moisture. It is further desirable that the connector has a small size, can provide a rapid connection and disconnection without special tools, and allows multiple connect and disconnect cycles without loss of function.

In many existing devices the connector is implemented in a molded header (insulating housing), formed from a hard medical grade polymer on the edge of the device's case, and the connector's receptacle contacts are connected to the feedthrough pins by discrete wiring, which is subsequently overmolded (covered and sealed by insulating material). The wiring must interface two dissimilar and spatially separated contact patterns and can be quite intricate. The assembly and the associated molding and testing can be labor intensive, as discussed in U.S. Pat. No. 7,274,963 (2007) to Spadgenske.

The header connectors for iso-diametric (having constant diameter) leads typically have blind lead receiving lumens (i.e., the lumens are open at one end only) into which a lead is inserted with significant force (adequate to generate contact forces and compress the seals), so lead insertion force and contact registration can be an issue. The header connectors are therefore more suitable for larger-diameter, lower-contact-count leads, such as those used with cardiac rhythm management devices, which can tolerate significant insertion force and have more liberal contact registration tolerances.

U.S. Pat. No. 6,321,126 (2001) to Kuzma shows a header connector design for flat-lead terminals. This patent addresses the need for a high contact count, small-dimensioned connector, but this design is only applicable to leads with flat lead terminals and cannot be adapted to iso-diametric lead terminals. In addition, the contact system appears to rely on an elastomeric backing of the lead terminal body for providing contact pressure. Since elastomeric materials are prone to time-dependent permanent deformation, contact pressure may relax with time, especially because such connections have a low compliance (independent of the elastic backing, the contacts have limited elastic deflection reserve). The low compliance is also problematic when repeated mating is required.

As the implantable medical devices and systems become more capable and number of the leads and the lead contact count and density increase, there is a need for small but robust connectors to make reliable connections to devices or components of the implantable system. The small size is especially important for devices such as neural and cochlear stimulators which are implanted in the cranium, both for medical reasons (a smaller cranial cavity needs to be created) and for aesthetic advantages. In such cases, it may be desirable to build the connector interface directly into the device's feedthrough housing cavity so that receptacle contacts are co-located with the feedthrough pins.

My U.S. Pat. No. 6,662,035 (2003) shows a feedthrough-based connector design intended for a device implantable beneath the scalp. This patent teaches how to implement reliable direct metal-to-metal connections between lead contacts and the corresponding feedthrough pins. The illustrative dimensions of the two-lead connector are a depth of approximately 6.5 mm, a length of approximately 15.0 mm, and a breadth of approximately 13.0 mm. These dimensions are still excessive for locating the connector on an edge of the device case or for use in size-critical subcutaneous applications, such as inside the cranium. Unfortunately, the size of the above feedthrough-based connector cannot be radically reduced due to the following factors:

(a) The device uses compressible contacts located entirely above the exterior (outwardly facing) surface of the feedthrough dielectric substrate, on which an interposer (seal) is seated. The entire compressible contact must be accommodated within the interposer thus adding to the total connector height.

(b) The compressible contacts use C-shaped springs having significant width and height that cannot be traded to reduce connector size. For a given spring-loop length, required for adequate contact force and deflection, a smaller contact height will lead to a greater contact width.

(c) The contact width controls the width of the interposer seal, and thus the connector's overall width.

(d) The spring contacts are free-standing and thus are susceptible to intra-operative handling damage if made too fragile. A smaller contact must be made from a thinner material (and thus would be more fragile) or it will be too stiff and have a low deflection capability. It is important that the contacts have adequate contact compliance or deflection range in order to accommodate assembly tolerances and to assure an adequate deflection reserve for repeated mating.

(e) A robust spring contact (necessary for the handling integrity) and a wide seal require substantial clamping hardware, including a relatively large screw. This larger screw causes the feedthrough area between the leads to be poorly utilized.

Another issue in miniature implantable connectors is protection of the implantable leads from handling damage, especially during intra-operative attachment of the leads to a connector. In order to protect the miniature implantable leads, the lead terminals may need to be pre-inserted into a lead-receiving connector component without significant insertion force. Subsequent handling can easily cause the leads to inadvertently retract prior to connector pressurization, causing a loss of contact registration.

SUMMARY

The present device, in one aspect, addresses the need for improved small implantable connectors built directly on a hermetic feedthrough of an implantable electronic device, such as a cochlear implant, a neurostimulator, a pacemaker, a pain-control device, and the like.

The connector in this aspect uses a contact system integrated with the feedthrough pin and a feedthrough housing as the sustaining structure for connector assembly and pressurization. The contact system consists of a feedthrough pin, a resilient compressible contact, and a means to position, secure, and protect the compressible contact.

Small connector size is realized by utilizing the feedthrough pin to directly interface, confine, protect, and precisely position the resilient contact element. The contact retention feature is provided by the feedthrough pin or by a separate component joined to the feedthrough pin.

A variety of compressible contacts can be used, including coil springs, fuzz buttons (a single length of a very fine wire formed into multiple small wavy loops), and metal-particle-filled elastomer buttons. These contact forms have been proven in many applications and can be economically produced in biocompatible versions. The compressible contacts may have a rigid tip provided by a conductive element in the form of a pin or a cup for a more robust contact point. The hard tip contact embodiments can also provide contact preloading, which helps to assure a consistent contact force.

The connector can be adapted to connect implantable leads with a variety of proximal lead terminals, including, but not limited to, iso-diametric terminals with tubular or ring contacts and flat terminals with planar contact pads.

In order to protect the miniature iso-diametric leads, a lead-proximal terminal is first inserted into a seal without encountering significant resistance. Once the lead is protected by the seal, the lead-seal assembly is subsequently lightly pressed into a cover or into a feedthrough cavity which retains and aligns the lead-seal assembly for the remaining steps of connector assembly and pressurization. Clamping options include space-efficient retention springs and clips.

DRAWINGS

Figure 1:
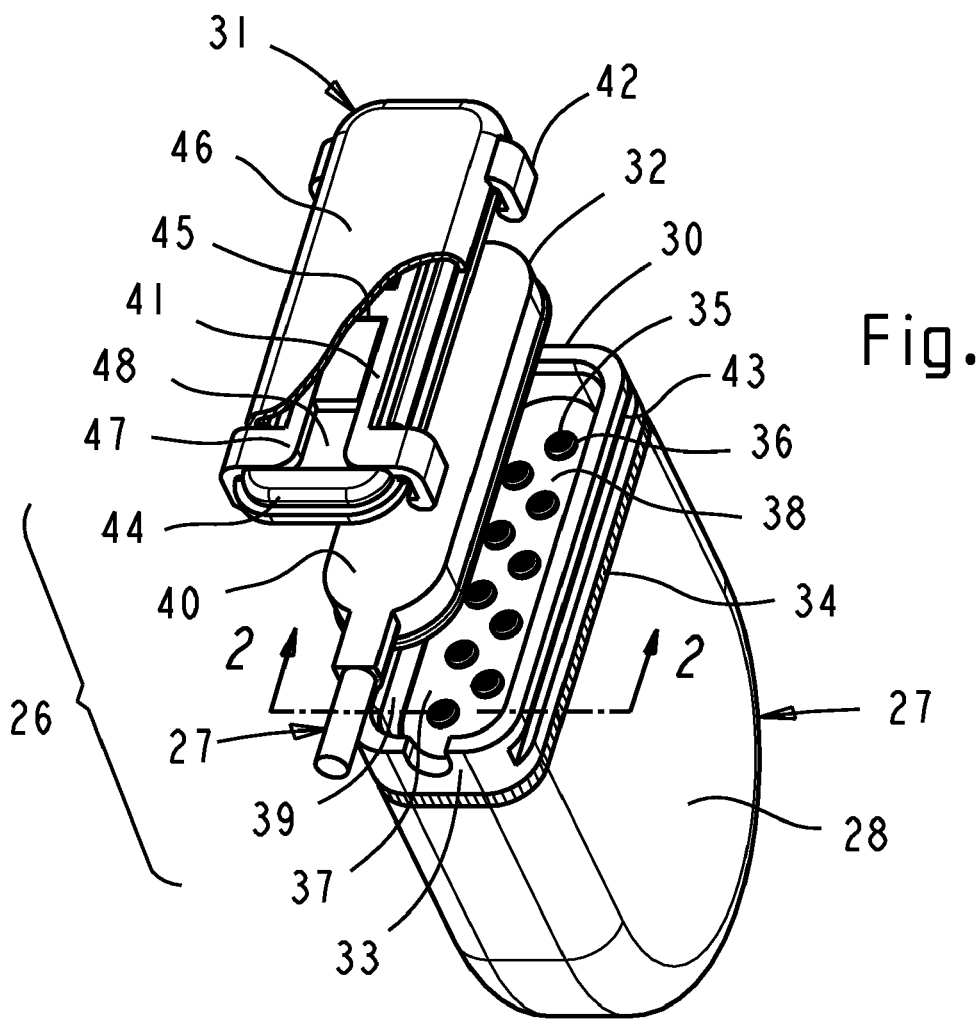
FIG. 1 is an exploded perspective view of an embodiment of the connector for leads with flat proximal terminals, showing a device feedthrough with integrated compressible contacts, the proximal end of the lead having a flat contact terminal, and a clamping cover.

| DRAWINGS - Reference Numerals | |
|---|---|
| 25 | device |
| 26 | connector |
| 27 | lead |
| 28 | case, device |
| 30 | feedthrough assembly |
| 31 | clamping cover |
| 32 | lead terminal, flat |
| 33 | feedthrough housing |
| 34 | weld line |
| 35 | compressible contact |
| 36 | feedthrough pin |
| 37 | feedthrough cavity |
| 38 | dielectric substrate |
| 39 | side wall, feedthrough cavity |
| 40 | lead terminal body |
| 41 | spring |
| 42 | latch |
| 43 | undercut, feedthrough housing |
| 44 | compression plate |
| 45 | mid-section, spring |
| 46 | cover, clamp |
| 47 | free end, spring |
| 48 | space |
| 50 | lead contact |
| 54 | feedthrough housing |
| 55 | welding flange |
| 56 | pressurization spring |
| 59 | feedthrough housing |
| 60 | feedthrough assembly |
| 61 | tubular section, feedthrough pin |
| 62 | outer end, compressible contact |
| 63 | inner end, compressible contact |
| 64 | rib, peripheral seal |
| 65 | latch |
| 66 | front end, retention spring |
| 67 | groove |
| 68 | back end, retention spring |
| 70 | connector |
| 71 | feedthrough assembly |
| 72 | compressible contact assembly |
| 73 | lead terminal |
| 74 | lead contact |
| 75 | seal |
| 76 | cover |
| 77 | clamping screw |
| 78 | seal lumen |
| 79 | channel |
| 80 | cover assembly |
| 81 | narrowing of channel |
| 82 | aperture, seal |
| 83 | alignment bosses |
| 84 | slotted hole |
| 85 | compressible contact |
| 86 | feedthrough pin |
| 87 | tubular section |
| 88 | dielectric substrate |
| 89 | top, compressible contact |
| 90 | rim, top of tubular section |
| 91 | exterior surface, substrate |
| 95 | connector |
| 96 | feedthrough assembly |
| 97 | compressible contact assembly |
| 98 | lead terminal |
| 99 | lead contact, tubular |
| 100 | seal |
| 101 | cover, clamping |
| 102 | retention clip |
| 103 | exterior cavity, feedthrough |
| 104 | dielectric substrate |

-continued

| DRAWINGS - Reference Numerals | |
|---|---|
| 105 | inside wall, feedthrough housing |
| 106 | seal lumen |
| 107 | latch |
| 108 | undercut |
| 109 | relief cut, cover |
| 110 | mid-section, undercut |
| 111 | compressible contact |
| 112 | rigid contact insert |
| 113 | collar, feedthrough pin |
| 114 | insert, retaining |
| 115 | tip, contact insert |
| 120 | connector |
| 121 | feedthrough assembly |
| 122 | feedthrough housing |
| 123 | lead terminal |
| 124 | lead contact, tubular |
| 125 | seal, dual lead |
| 126 | cover, clamping |
| 127 | retention clip |
| 128 | exterior cavity, feedthrough |
| 129 | dielectric substrate |
| 130 | inside wall, feedthrough |
| 131 | seal lumen |
| 132 | latch |
| 133 | undercut |
| 134 | relief cut, cover |
| 135 | mid-section undercut. |
| 140 | seal, Ω-profiled |
| 141 | cover, clamping |
| 142 | Ω-profiled channel |
| 143 | cover protrusion |
| 147 | spring sleeve |
| 150 | compressible contact |
| 151 | feedthrough pin |
| 152 | tubular section, feedthrough pin |
| 155 | compressible contact |
| 156 | plunger |
| 157 | hat, snap-on |
| 158 | dimple |
| 159 | feedthrough pin |
| 160 | contact top |
| 161 | compressible contact |
| 162 | hat |
| 163 | dimple |
| 164 | feedthrough pin |
| 170 | compressible contact, coil spring |
| 171 | hat |
| 172 | feedthrough pin |
| 173 | nail head |
| 174 | hole |
| 175 | end, spring |
| 180 | feedthrough pin |
| 181 | tubular section |
| 182 | compressible contact |
| 183 | bottom, dielectric substrate |
| 184 | crimp, feedthrough pin |
| 190 | compressible contact |
| 191 | contact tip insert |
| 192 | shank |
| 193 | shoulder |
| 194 | weld |

DETAILED DESCRIPTION

FIGS. 1-4—Embodiments for Leads with Flat Terminals

FIG. 1 is an exploded perspective view of an implantable device 25 with a connector 26 for detachably connecting an electrode lead 27 to the device's electronic circuitry contained in a hermetically sealed case 28.

Device 25 is designed to be implanted subcutaneously and/or in a body cavity, typically in a chest or in a cranium.

The lead has multiple conductors (not shown) and extends from the device (proximal end) to the tissue targeted for sensing and/or stimulation (distal end), where the conductors connect to the lead's sensing and/or stimulating electrodes (not shown).

The connector's functional parts include a hermetic electrical feedthrough 30, a clamping cover 31, and a lead terminal 32. A separable mating interface is built directly into a hermetic feedthrough housing 33, which is attached to case 28 along a weld line 34. The connector mating interface has an array of compressible contacts 35 integrated with feedthrough pins 36 of feedthrough 30. (Only the top of pin 36 is shown in FIG. 1, but one is shown cross-sectioned in FIG. 2.) The mating ends or tips of compressible contacts protrude into a feedthrough exterior cavity 37 which is defined by the exterior side of a dielectric substrate 38 and inside walls 39 of housing 33.

Lead terminal 32 has a paddle-shaped body 40 with an array of contact pads 50 (FIG. 2) which are connected to the respective conductors of lead 27, and are disposed in a pattern directly mapped to the corresponding array of feedthrough pins 36. The terminal body cooperates with feedthrough exterior cavity 37 to align the array of compressible contacts 35 with the corresponding array of contact pads 50, and to provide contact electrical isolation seals.

Clamping cover assembly 31 has a captive spring 41 which provides engagement latches 42 for disengageably locking the clamping cover against undercuts 43 on the outside walls of feedthrough housing 33. The spring can be attached to compression plate 44 at mid-section 45, e.g., by laser welding, and capped with an optional snap-on cover 46, preferably made out of bio-compatible polymer. The latches can be disengaged by spreading the springs outwardly at free ends 47, using a simple tool such as screwdriver in space 48 between the spring free ends. The spring can be stamped or machined from a biocompatible springy alloy, such as titanium alloy 6Al-4V. The compression plate can also be made from titanium or a titanium alloy. The optional cover can be molded from a biocompatible polymer or a medical grade elastomer if desirable. Alternatively, the top cover can be made out of a hard polymer or a metal and joined to the compression plate along its perimeter. The thus contained spring can be actuated through openings in the cover, e.g., using a built-in actuating cam between the spring's free ends (not shown).

Figure 2:
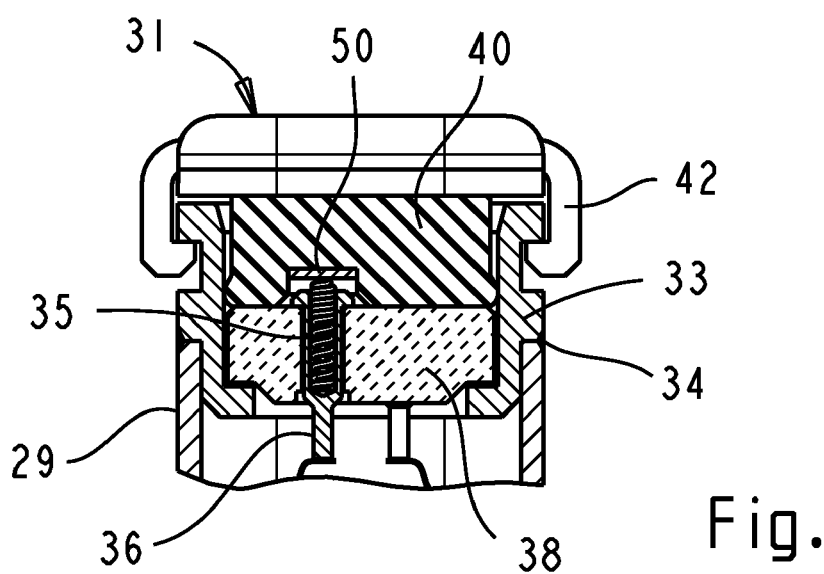
FIG. 2 is a partial cross-sectional view of the pressurized connector of FIG. 1.

When connector is assembled as shown in FIG. 2, it is pressurized, i.e., compressible contacts 35 are compressed to provide contact pressure and the seals on lead terminal body 40 are compressed between pressure plate 44 and dielectric substrate 38 to provide sealing. When contacts 35 are compressed they electrically connect the corresponding lead contacts 50 to feedthrough pins 36, which extend into the interior of case 28 and connect to the electronics (not shown) inside device case 28. Concurrent with contact pressurization, the integral seals on the lead terminal body are compressed to seal the terminal body against the exterior surface of dielectric substrate 38 (interfacial seal) and against side walls 39 of the feedthrough cavity (peripheral seal). This seal system isolates the adjacent and non-common electrical connections from each other and from other conductive components, such as housing 33, and protects the connector interface from ingression of body fluids, which also tend to be conductive.

Figure 3:
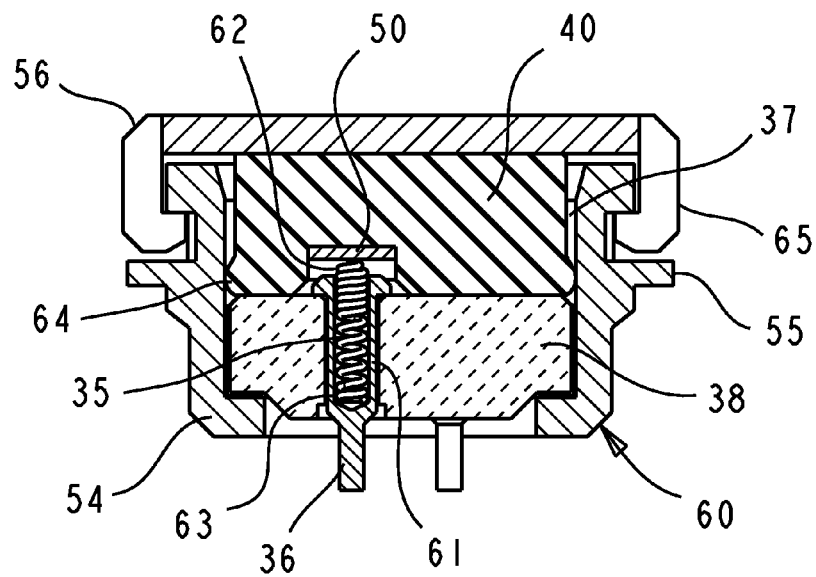
FIG. 3 is a cross-sectional view of a variation of the connector shown in FIG. 2, taken as indicated by the lines 2-2 of FIG. 1, with a planar welding flange and alternate clamping means.

FIG. 3 shows a connector assembly with the same contact system, feedthrough cavity, and lead terminal as shown in FIG. 2. For illustrative purposes, feedthrough housing 54 has a welding flange 55, adapted for attaching the feedthrough on a face (rather than on an edge) of the device's case. After attachment, welding flange 55 becomes coplanar with the large surface of the case (not shown). Also in this embodiment, an alternative connector clamping means—a pressurization spring 56—is shown, which can be used interchangeably with the clamping cover described in connection with FIG. 2.

Feedthrough assembly 60 comprises dielectric substrate 38, housing 54, and feedthrough pins 36. These components are made from biocompatible materials, assembled as shown in FIG. 3, and joined by brazing using a biocompatible braze. The medical feedthrough materials and assembly techniques are well known in the art and are discussed in more detail in published US Patent Application 2007/0134985 A1 to Frysz et al. Currently preferred but non-limiting examples of materials include Ti and Ti alloys for the housing, highly purified aluminum oxide (pure alumina ceramic) for the dielectric substrate, platinum and platinum-iridium alloys for the feedthrough pins, and pure gold for brazing.

The contact system and its advantages will be now described in more detail. Feedthrough pin 36 has a tubular section 61, into which compressible contact 35 is installed. The tubular section of the pin resides substantially within the thickness of dielectric substrate 38, in which the pin is hermetically sealed. The tubular section can be obtained by drilling a blind hole in the feedthrough pin. Alternatively, the feedthrough pin can be a deep-drawn part or can be made out of tubing with one end hermetically sealed by crimping and/ or welding. Compressible contact 35 is a miniature coil spring, and is protectively confined in tubular section 61. Only outer tip 62 extends from the tubular section to assure necessary contact compliance or deflection when connector is mated.

If the designer prefers to use a longer compressible contact, e.g., to increase contact deflection range or to further reduce compressible contact radial dimensions, the tubular section can be extended beyond the interior side of the dielectric substrate (into the device interior), without increasing the overall height of the connector. The compressible contact extension from the tubular section or the elevation of the contact tip above the exterior surface of dielectric substrate need not change when the contact spring is made longer. The coil spring contact has a variable pitch and a variable outside diameter. An outer end 62 of coil spring contact 35 is tightly wound to form a contact tip. The tightly wound top coils can be further joined together (e.g. by welding) or reinforced by adding a rigid tip insert. An opposite inner end 63 of the coil spring may have at least one coil with an outside diameter slightly larger than the inside diameter of the tubular section so that the coil spring can be pressed into the tubular opening of the feedthrough pin and retained therein by the radial interference. Alternatively, the inner end (near the bottom) of the tubular opening can have a necking or a slightly reduced diameter to provide an interference fit with the inner end of the contact spring.

The compressible contact can be made using known equipment and manufacturing techniques employed in fabrication of miniature coil springs for pogo pins used in electrical test sockets. The miniature coil spring can be made from a high strength biocompatible alloy, such as 80Pt-20Ir platinum-iridium alloy, which can be drawn into a high strength fine wire with a good formability.

Feedthrough 60 has cavity 37, formed by the exterior side of dielectric substrate 38 and the inside walls of the feedthrough housing 54. This cavity accommodates flat lead terminal 33 (FIG. 1) having body 40. Terminal 35 has an array of lead contact pads 50, which are the termini of the respective lead conductors. The lead body is molded from a medical silicone polymer, so that it can provide integral seal features. The lead contacts are recessed in lead terminal body 40 to allow the bottom surface of the terminal body to serve as a seal against the exterior surface of dielectric substrate 38. In addition to the inter-facial seal against the ceramic surface, the sides of the terminal body can provide a perimeter seal against feedthrough cavity side walls. Integral rib 64 can be added to the side perimeter of the terminal body to enhance the peripheral seal. Similarly, the bottom sealing surface of the terminal body may have ribs or rings to optimize seal effectiveness and/or to lower the required seal compression force. The integral seals are preferred, but a separate seal, interposed between the body of the lead terminal and the exterior surface of the dielectric substrate, can be used instead.

When the terminal is inserted into the feedthrough cavity, the compressible contacts align with the respective lead contacts of the lead terminal. Preferably, the terminal is inserted into the feedthrough cavity with a slight interference, which initiates the peripheral seal and securely retains the terminal in the feedthrough cavity for the remaining assembly steps.

Figures 4A, 4B:
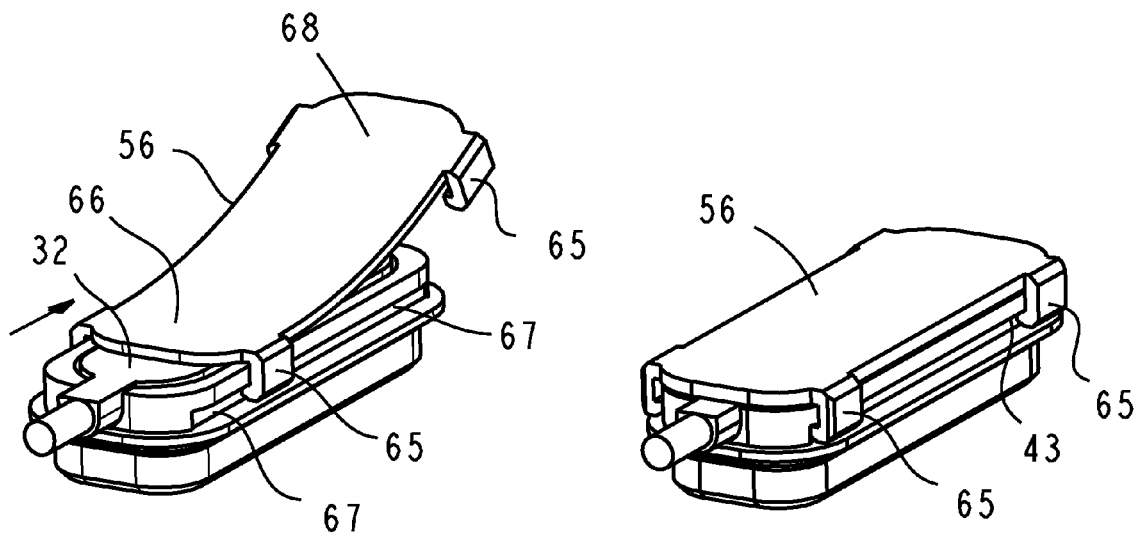
FIG. 4A is a perspective view of the connector of FIG. 3 with a pressurization spring partially engaged.
FIG. 4B is a perspective view of the connector of FIG. 3 with the pressurization spring fully engaged.

Pressurization spring 56 with engagement latches 65 can be applied as shown in FIGS. 4A and 4B. First, a pair of latches 65 on the first (front) end 66 of the clip is engaged with grooves 67 from the front end of the feedthrough. After sliding the retention spring toward back in the direction of the arrow to the position shown in FIG. 4A, a second (back) end 68 of the spring is pressed down until the other two latches line up with grooves 67 on the back side of the feedthrough. The spring is then pushed toward front to the final position shown in FIG. 4B. As the spring is engaged against undercuts 43 formed by grooves 67, the spring exerts pressure against top surface of lead terminal body 40, forcing the lead terminal contact pads to make pressure connections with the corresponding compressible contacts and concurrently compressing the seals.

The spring can be made from a high strength biocompatible alloy such as titanium alloy 6Al-4V. The top surface of the lead terminal body on which the retention spring slides may incorporate a low-friction polymeric lining or a coating, such as a poly-para-xylylene (sold under the trademark Parylene by Specialty Coating Systems, Indianapolis, Ind.), to reduce sliding friction between the two components.

The connector's small size is attained by confining the compressible contact in the tubular section of the feedthrough pin, so that the compressible contact resides substantially within the thickness of the dielectric substrate, defined by the exterior and interior surfaces of the substrate. The compressible contact can thus be made longer in order to reduce the contact's radial or cross-sectional dimensions without impacting connector height. The small radial dimensions of the compressible contacts and the small effective contact height (the elevation above the exterior surface of the dielectric substrate) enable low profile connectors with closely spaced contacts. A large number of connections can thus be provided in a small connector volume. The exemplary device shown in FIG. 1 can be less than 5 mm thick and the total height of the connector assembly, including the feedthrough, can be less than 4 mm.

FIGS. 5-10—First Embodiment for Leads with Iso-Diametric Terminals

Figure 5:
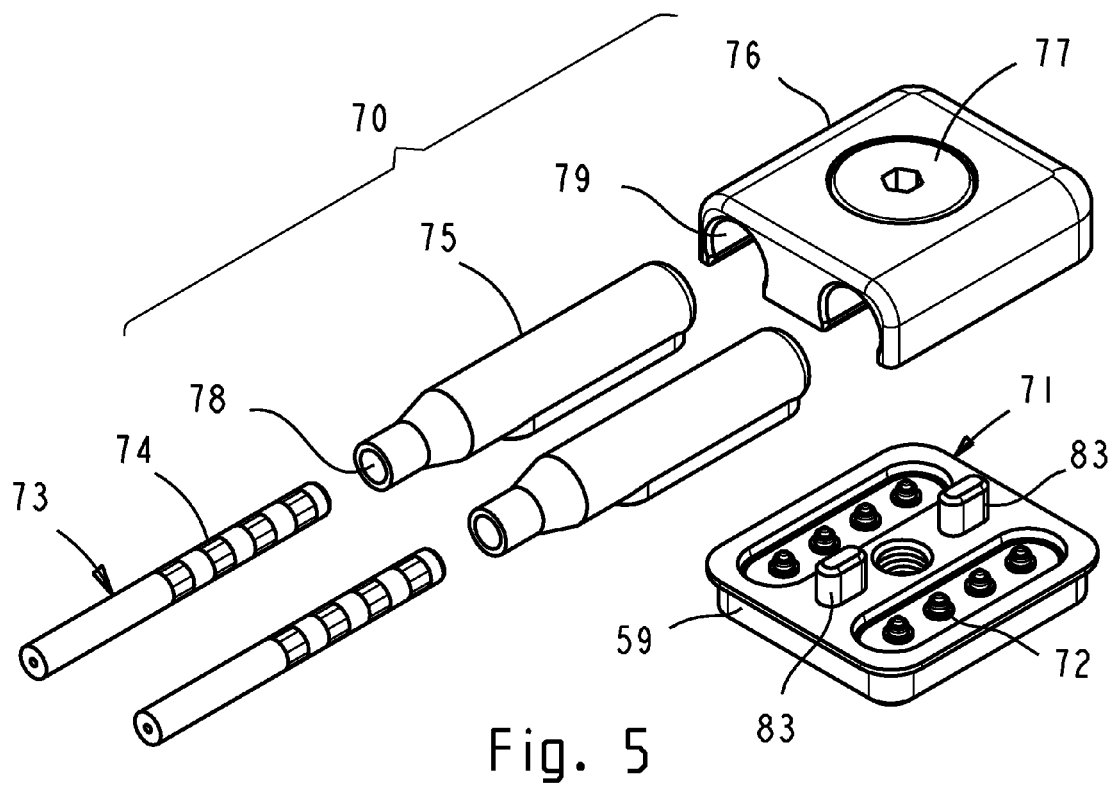
FIG. 5 is an exploded perspective view of an embodiment of the connector for connecting iso-diametric leads where lead terminals are pre-inserted into the seals and subsequently inserted into the cover where they are retained prior to connector pressurization.

FIG. 5 shows an exploded perspective view of an implantable connector 70 for leads with iso-diametric proximal terminals. This connector has (a) compressible contacts integrated with feedthrough pins; (b) a seal into which the lead terminal is inserted without significant interference, (c) a cover and/or a feedthrough cavity into which the lead-seal assembly is inserted with or without interference; and (d) a clamping or pressurization means such as a clamping cover secured to the feedthrough housing with a clip, a latching spring, or a screw.

Connector 70 has a hermetic feedthrough assembly 71 with compressible contact assemblies 72, lead end terminals 73 with lead contacts 74, seals 75, a pressurization cover 76, and a clamping screw 77.

In this embodiment, the lead-seal assembly is preassembled in the clamping cover prior to connector pressurization. The clamping cover can be fabricated from a biocompatible material such as titanium or titanium alloy or a hard polymer such as polyetheretherketone PEEK, preferably reinforced (e.g. filled with carbon fibers to increase strength and stiffness). Implantable-grade PEEK, also known as PEEK-OPTIMA is available from Invibio, Inc. Ceramic materials such as pure alumina or toughened alumina are also suitable cover materials.

A desirable method of assembly of connector 70 is to first insert each lead terminal into circular lumen 78 of respective seal 75 without significant interference (preferably with less than 1 Newton (N) axial insertion force). Once the lead is protected in the seal, the lead-seal assembly is inserted into channel 79 in cover 76, preferably with a slight interference, to obtain lead-seal-cover assembly 80 shown in FIG. 6. The retention of the lead-seal assembly in the cover by the slight interference fit prevents inadvertent dislocation of the lead in the cover assembly. In addition, the profile of the channel is Ω-shaped, with narrowing at 81. This further prevents dislodging of the lead-seal assembly in the radial direction. These retention features are advantageous since they assure secure holding of the components in the cover through the remaining assembly steps. The lead contact registration in the cover assembly can be visually verified via seal apertures 82 and reliably maintained.

An additional advantage of the present assembly method is that the radial pressure from the interference fit between the lead-seal assembly and the cover is communicated to the lead-seal interface and thus initiates the seal between lead electrode contacts. The initial seal preload excludes fluids from critical seal areas during connector installation and reduces the total clamping force required for connector pressurization.

In the final assembly step, the lead-seal-cover assembly is aligned with feedthrough 71 using alignment bosses 83 in feedthrough housing 59 and the corresponding slotted holes 84 in cover 76. The connector is fully mated by clamping cover 76 to feedthrough housing 59 with screw 77. The assembled connector is shown in FIG. 7.

Figures 6, 7:
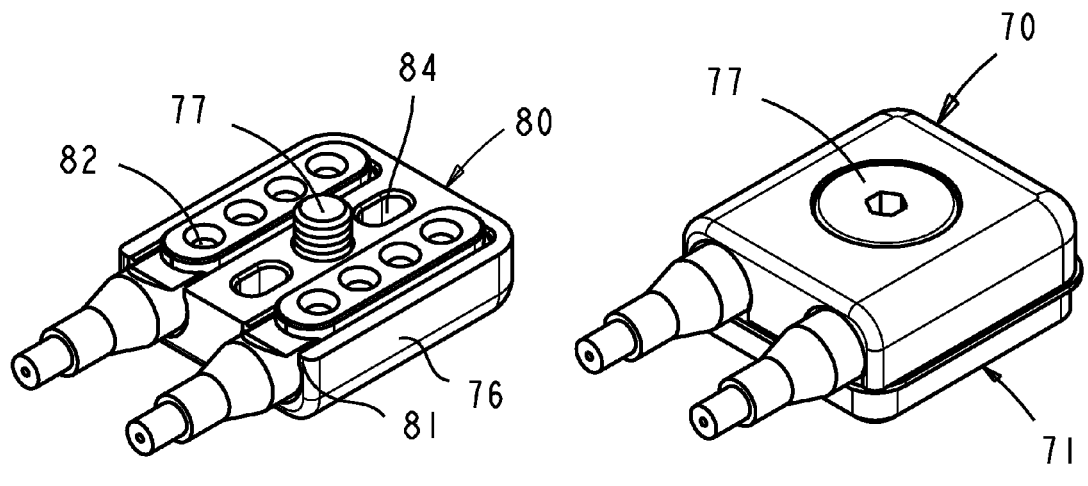
FIG. 6 is a perspective view of the connector cover with the lead-seal assembly installed.
FIG. 7 is a perspective view of the fully assembled (pressurized) connector of FIG. 5.
Figure 8:
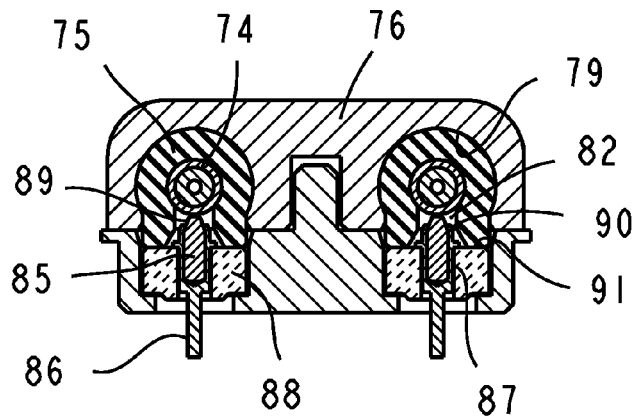
FIG. 8 is a cross-sectional view of the connector of FIG. 7 taken through the contacts, in a plane normal to the leads, as indicated by the line 8-8 of FIG. 9.

FIG. 8 is a cross-sectional view of the mated connector of FIG. 7, taken through the contacts, in the plane normal to the lead.

The connector uses compressible coil spring contacts 85 (similar to contact 35 of FIG. 3). Alternatively, a conductive button such as a platinum-iridium fuzz button, or a metal-particle-filled conductive elastomer button can be used. The compressible contact is enclosed in tubular section 87 of feedthrough pin 86. The tubular section of the pin resides substantially within the thickness of dielectric substrate 88 in which the pin is hermetically sealed. The compressible contact has a tapered outer end 89 and can be retained in the tubular section by a rolled or crimped rim 90 at the top of the tubular section. The rim is rolled or crimped after the compressible contact is inserted into the tubular section. Alternatively, an inwardly rolled rim can be pre-fabricated prior to the feedthrough assembly to allow a compressible button to be forced through the rim and snap-back in the tubular section.

The compressible contacts electrically connect lead contacts 74 to the corresponding feedthrough pins 86 which, in turn, connect to the device's electronics contained in the device's case (not shown). The compression of the seals between the inner surfaces of cover channels 79 and exterior surface 91 of dielectric substrate 88 completes electrical isolation between adjacent contacts and isolates the contacts from other non-common conductive components and from ambient body fluids or fluids that may be used to rinse the implantable components intra-operatively.

Figure 9:
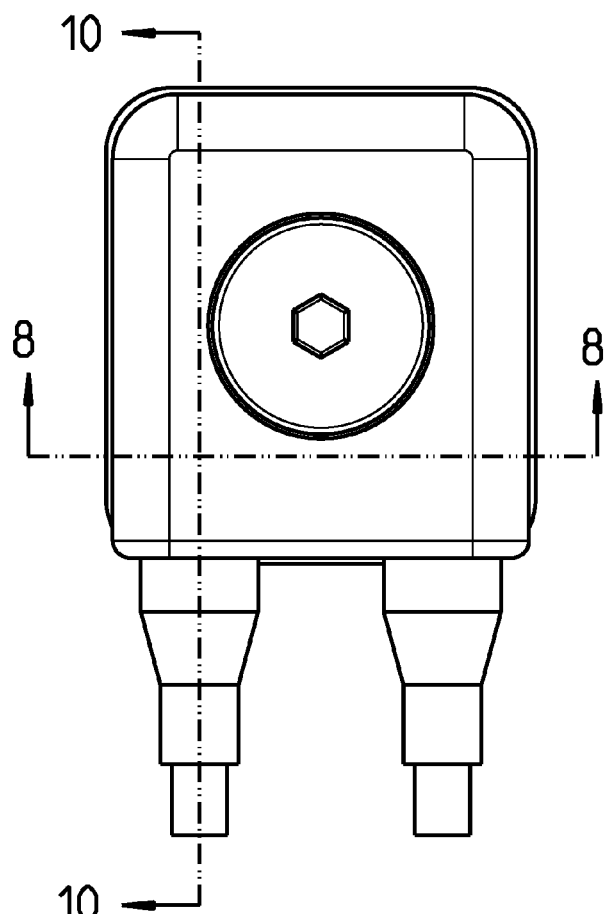
FIG. 9 is a top view of the connector of FIG. 7.
Figure 10:
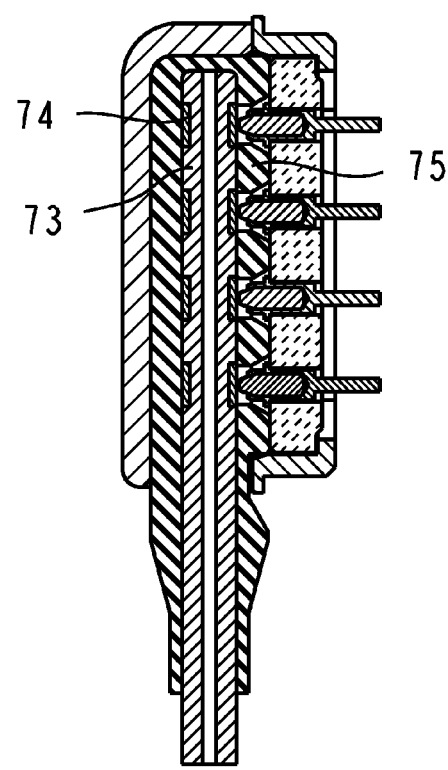
FIG. 10 is a cross-sectional view of the connector of FIG. 7 taken through contacts, along the lead axis, as indicated by the line 8-8 of FIG. 9.

FIG. 9 is a top view of the connector of FIG. 7, which serves as a reference for the cross-sectional views of FIGS. 8 and 10.

FIG. 10 is a cross-sectional view of the assembled connector of FIG. 9, taken along the lead. This view illustrates how inter-contact seal between adjacent contacts is accomplished by compressive radial pressure on seal 75 around the insulated portion of lead 73, between tubular contacts 74.

Figure 11:
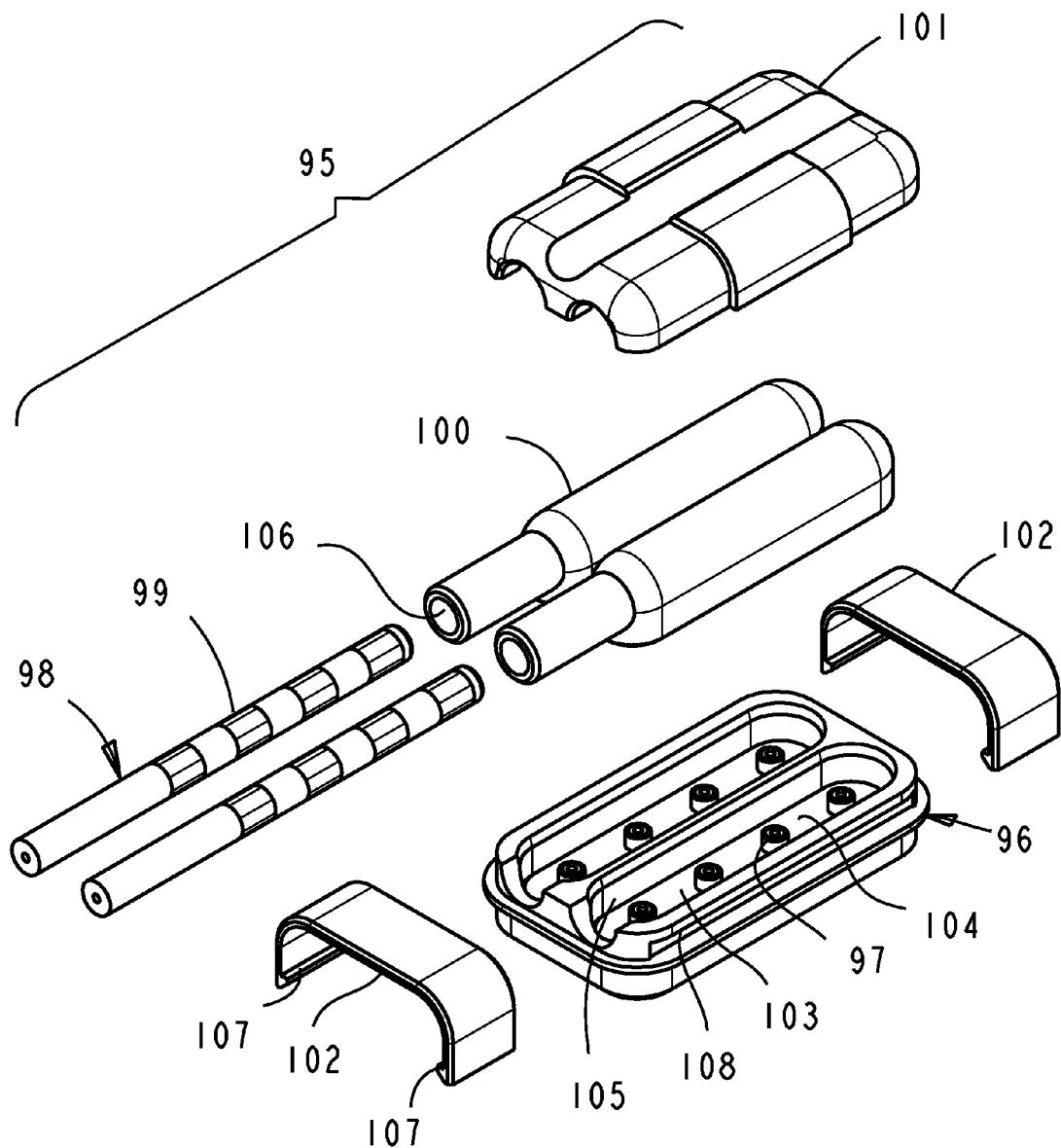
FIG. 11 is an exploded perspective view of the connector for iso-diametric leads, where lead terminals are pre-inserted into the seals and subsequently inserted into the feedthrough cavity prior to connector pressurization.
Figure 12:
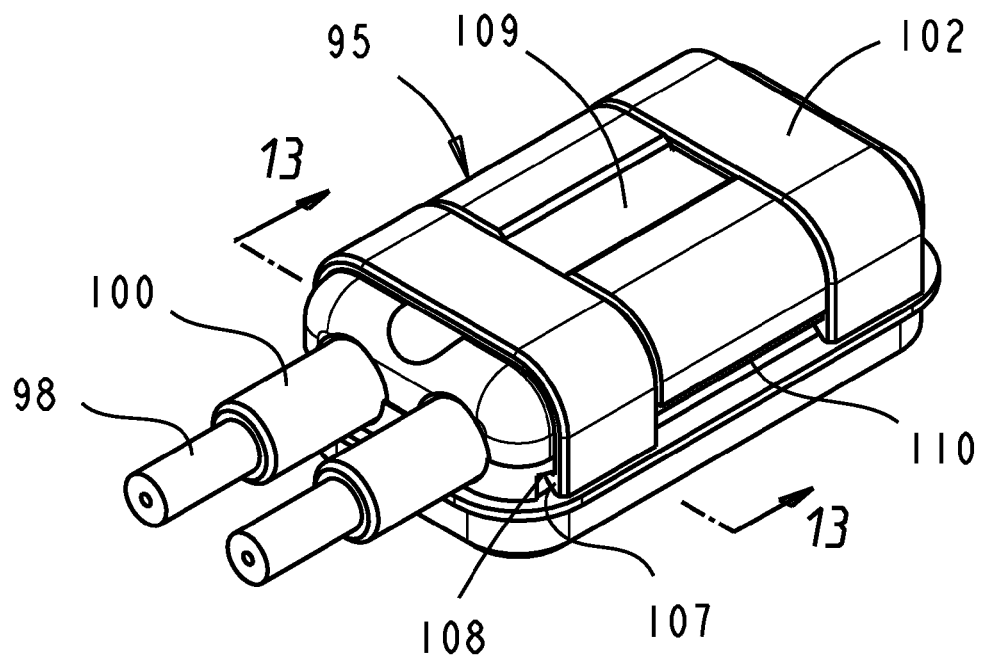
FIG. 12 is a perspective view of the fully assembled (pressurized) connector of FIG. 11.
Figure 13:
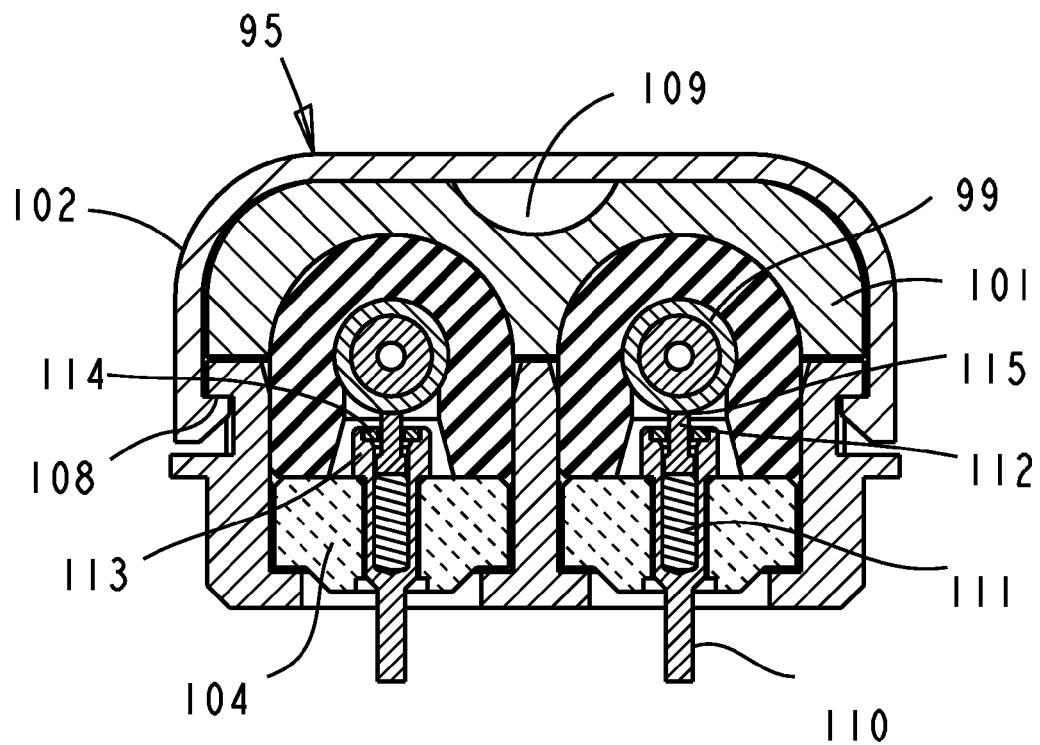
FIG. 13 is a cross-sectional view of the connector of FIG. 12, taken through the contacts, in the plane normal to the leads, as indicated by the line 13-13 of FIG. 12.

FIGS. 11-13—Second Embodiment for Leads with Iso-Diametric Terminals

FIG. 11 is an exploded perspective view of a connector 95 which has a hermetic feedthrough assembly 96 with compressible contact assemblies 97, lead terminals 98 with tubular contacts 99, seals 100, a clamping cover 101, and U-shaped retention clips 102. The feedthrough has a cavity 103, bound by the surface of a dielectric substrate 104 and inside walls 105 of the feedthrough housing.

In order to assemble connector 95, the proximal terminal of each lead 98 is first inserted into a respective circular lumen 106 of seal 100 without significant interference (preferably less than 1 N axial insertion force). Once the lead terminal is protected by the seal, the lead-seal assembly is inserted into feedthrough cavity 103, preferably with slight interference. The slight interference is advantageous since it assures secure holding of the lead-seal assembly in the feedthrough cavity through the final steps of connector assembly. In addition, compression of the seal in the feedthrough cavity initiates inter-contact and peripheral seals. Thus obtained feedthrough-seal-lead assembly is pressurized by securing clamping cover 101 with clips 102. Clip latches 107 cooperate with undercuts 108 on the outside of the feedthrough housing to maintain connector pressurization.

FIG. 12 is a perspective view of the fully assembled connector 95. Retention clip latches 107 engage undercuts 108 on the sides of the feedthrough housing, thus maintaining connector in the pressurized or mated state. Relief cut 109 on the top of the clamping cover can be used for insertion of a stylet (to increase tension on the clip) and/or for aiding in removal of clips with a surgical tool.

If desired, a simple clamping tool (not shown) can be used to temporarily clamp the connector in order to facilitate installation and/or removal of the clips. Feedthrough undercuts 108 can be extended throughout feedthrough housing length (as shown) so that the temporary clamping tool can engage the feedthrough undercuts at mid-sections 110 and force the cover down with a quick action screw or cam.

FIG. 13 is a cross-sectional view of the mated connector of FIG. 12 taken through the contacts in the plane normal to the lead. Compressible contact 111 is a coil spring or a conductive button such as a fuzz button or a metal-particle-filled elastomer button. Rigid conductive insert 112 provides the contact tip (contact point) for connecting to the lead tubular contact. The compressible contact and the rigid conductive insert are retained in the tubular section of the feedthrough pin by a washer-like insert 114, attached to the top of a feedthrough pin collar 113, preferably by laser welding. The compressible contact is preloaded (pre-compressed) by insert 114 to provide desirable contact characteristics (lower contact force variation). Alternatively the rim can be made thinner so that it can be crimped or rolled inwardly (as is rim 90 in FIG. 8) to retain the compressible contact and the rigid tip insert under internal preload.

In addition to providing a more consistent contact force, this implementation of the contact provides a robust contact tip 115. The rigid tip can be flat, rounded, or tapered, and may have one or more surface cuts, such as V-slots, to provide pointed contact features for a low resistance connection with lead contact 99.

Figure 14:
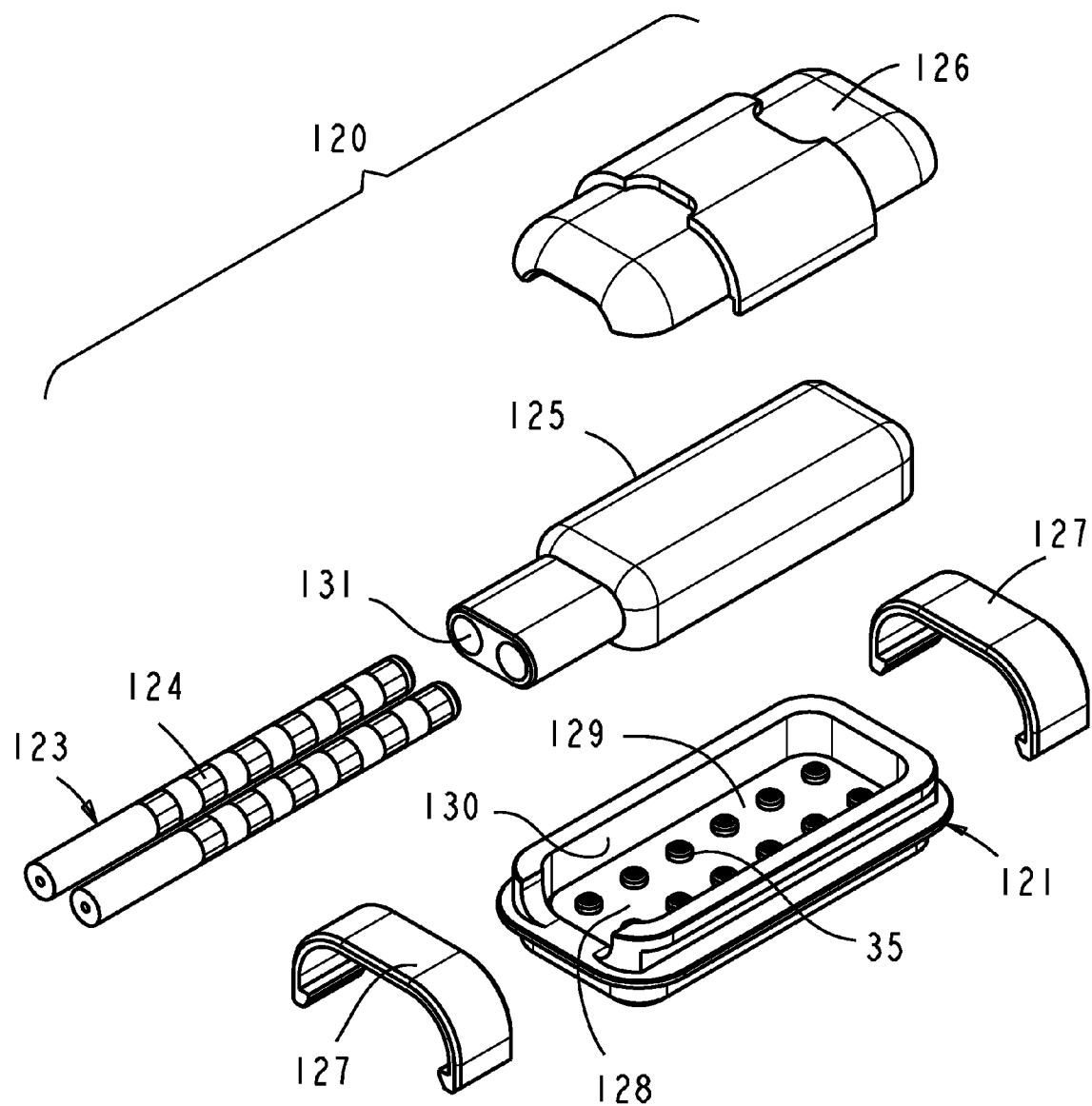
FIG. 14 is an exploded perspective view of the connector with a dual-lead seal and a single feedthrough cavity.
Figure 15:
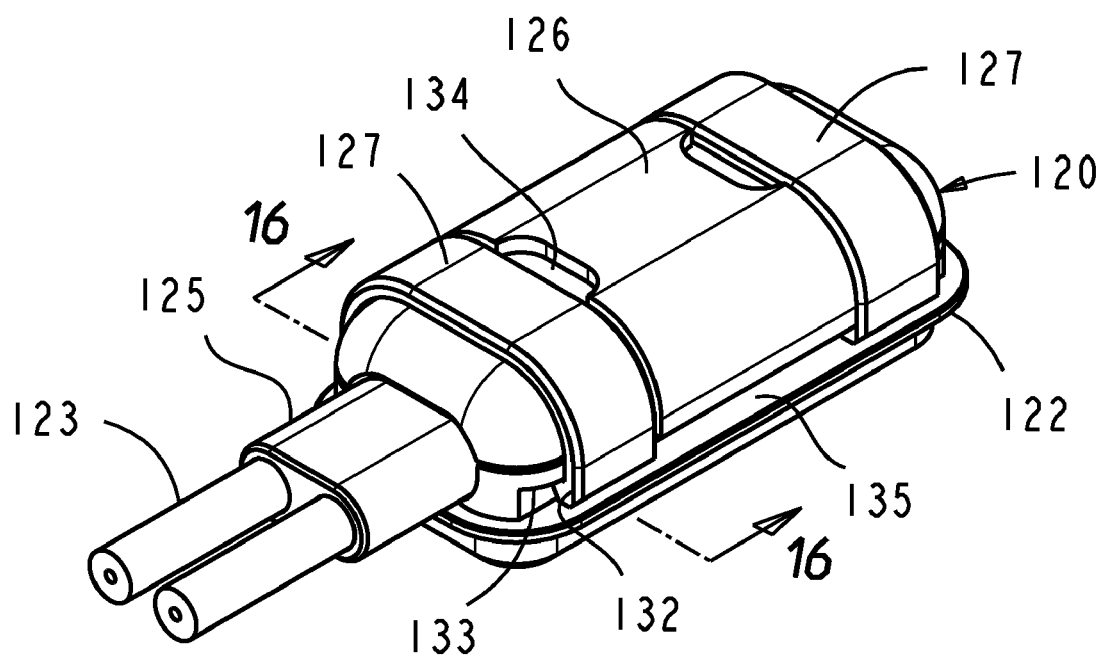
FIG. 15 is a perspective view of the fully assembled (pressurized) connector of FIG. 14.
Figure 16:
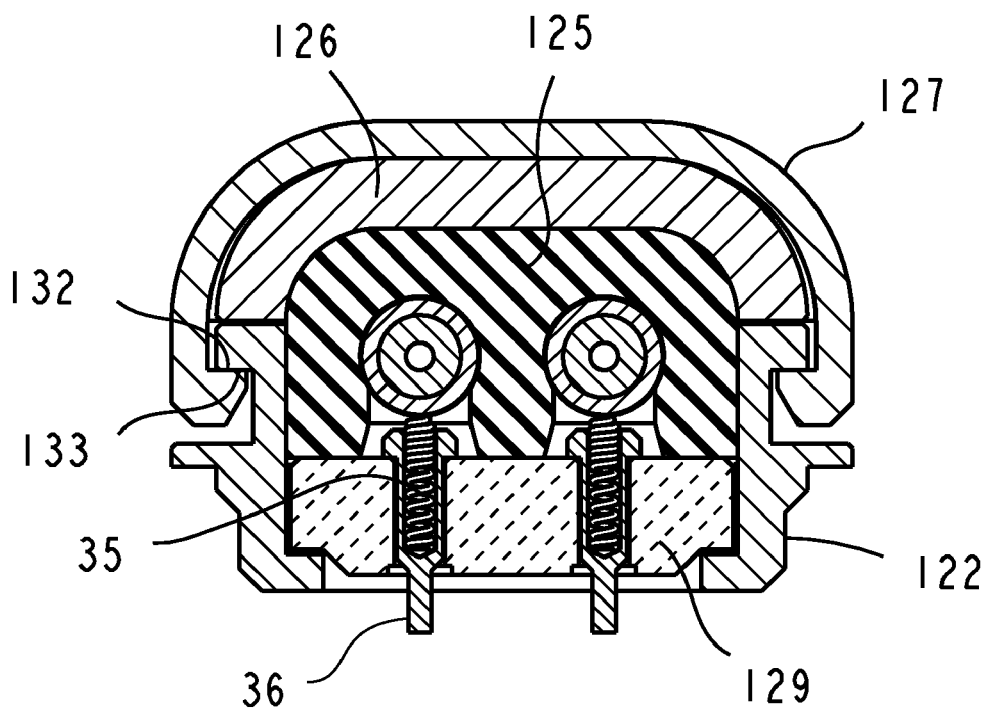
FIG. 16 is a cross-sectional view of the connector of FIG. 15, taken through the contacts, in a plane normal to the leads.

FIGS. 14-16—Third Embodiment for Leads with Iso-Diametric Terminals

FIG. 14 is an exploded perspective view of connector 120, which has hermetic feedthrough 121 with compressible contacts 35, lead terminals 123 with contacts 124, seals 125, clamping cover 126, and retention clips 127. The feedthrough has an exterior cavity 128, bound by top surface of a dielectric substrate 129 and inside walls 130 of a feedthrough housing 122. These are the same functional components as in connector 95 of FIG. 11 and the same assembly method is applicable. However, while connector 95 has a separate seal for each lead and a separate feedthrough cavity for each seal-lead assembly, connector 120 has a single seal 125 with two lead-receiving lumens side-by-side so that two leads are accommodated in a single seal. Each lead terminal 123 is received into respective seal lumen 131, and the dual lead-seal assembly is accommodated in a single feedthrough cavity 128. These and other differences, such as contact design, number of contacts per lead, and contact spacing, illustrate how these features can be used interchangeably in various connector embodiments.

FIG. 15 is a perspective view of the fully assembled connector 120. Retention clip latches 132 engage undercuts 133 on the outside of the feedthrough housing 122, thus maintaining the connector in the mated state. Relief cuts 134 on the top of clamping cover 126 can be used for aiding in removal of clips with a screwdriver a surgical tool.

If desired, a simple clamping tool (not shown) can be used to temporarily clamp the connector in order to facilitate installation and/or removal of the clips. Feedthrough undercuts 133 continue along the feedthrough length so that the latches of the temporary clamping tool could engage the feedthrough undercuts at mid-sections 135 and force the cover down with a quick action screw or cam. After the retention clips are installed the temporary tool is removed.

FIG. 16 is a cross-sectional view of the mated connector of FIG. 15 taken through the contacts in the plane normal to the lead. Compressible contact 35 is a coil spring retained in feedthrough pin 36 as described earlier.

FIGS. 17-22—Additional Embodiments for Leads with Iso-Diametric Terminals

Figure 17:
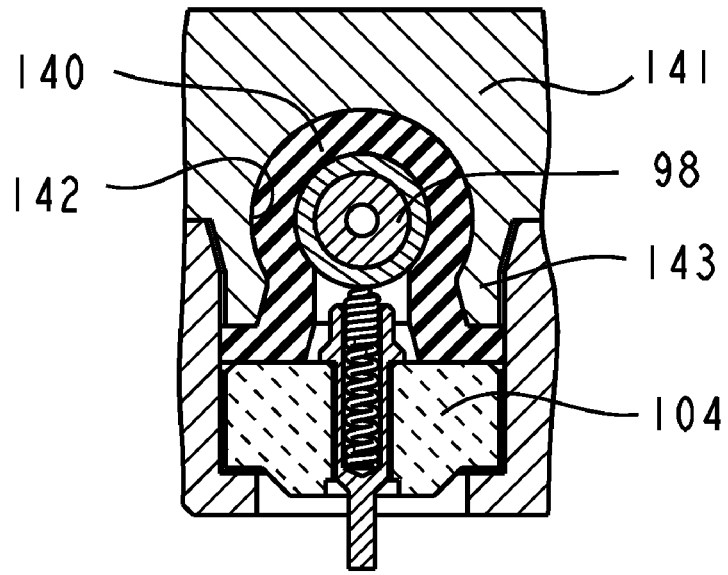
FIG. 17 is a variation of cross-sectional view of FIG. 13, taken as indicated by the lines 13-13 of FIG. 12, where an Ω-profiled seal is retained in cover protrusions extending into the feedthrough cavity.

FIG. 17 is a partial cross-sectional view of a mated connector, which is a variation of the connector shown in cross-sectional view of FIG. 13. The assembly of lead terminal 98 and a Ω-profiled seal 140 is retained in a complementarily profiled channel 142 in cover 141. The cover has protrusions 143 extending into the feedthrough cavity, which guide the cover assembly into the feedthrough during assembly and pressurization.

Figure 18:
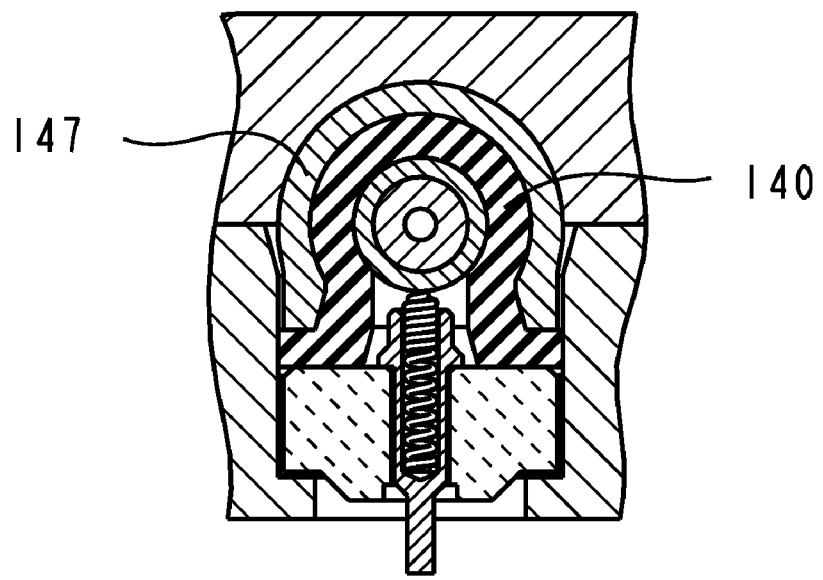
FIG. 18 is a variation of cross-sectional view of FIG. 17 where the Ω-profiled seal is retained in a C-profiled springy sleeve.

FIG. 18 is a variation of the connector shown in cross-sectional view of FIG. 17. The assembly of lead terminal 98 and Ω-profiled seal 140 is inserted into a C-profiled spring sleeve 147 prior to insertion into the feedthrough cavity. The spring sleeve activates the inter-contact seals prior to full connector pressurization. Pre-pressurization of the inter-contact seal by the spring sleeve reduces the pressurization load that needs to be applied through the cover.

FIGS. 19 through 22 show additional embodiments of compressible contacts which can be used interchangeably with those already discussed.

Figure 19:
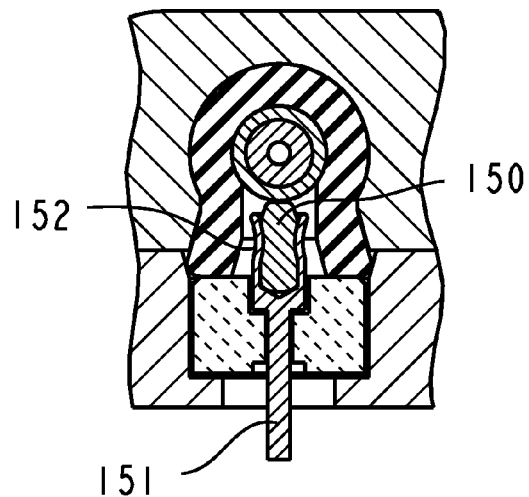
FIG. 19 is a variation of cross-sectional view of FIG. 8, taken as indicated by the lines 8-8 of FIG. 9, where the compressible contact is a conductive button retained in a profiled tubular opening of the feedthrough pin.

FIG. 19 is a partial cross-sectional view of a connector which is a variation of the connector shown in cross-sectional view of FIG. 8. A compressible contact 150 can be a fuzz button or a metal-particle-filled elastomer button. The compressible conductive button is protectively confined and retained in a profiled tubular section 152 of a feedthrough pin 151. The tubular opening has an hourglass profile which helps to retain the contact by compressing the contact at the narrow diameter necking and allowing the contact to expand at the larger diameter below.

Figure 20:
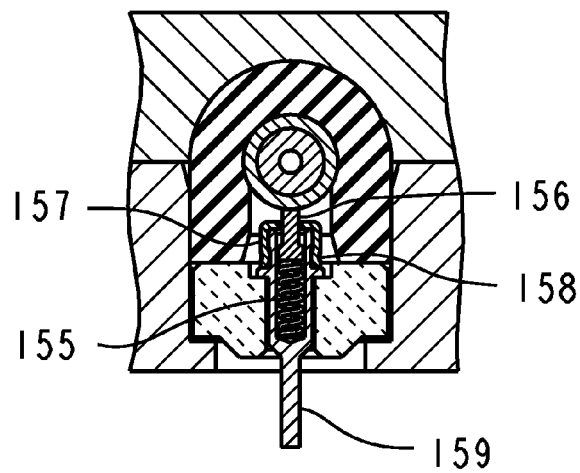
FIG. 20 is a variation of cross-sectional view of FIG. 13, taken as indicated by the lines 13-13 of FIG. 12, where the compressible contact is a coil spring, secured and preloaded by a cylindrical hat attached to the feedthrough pin.

FIG. 20 is a partial cross-sectional view of a connector which is a variation of the connector shown in cross-sectional view of FIG. 13. The contact assembly includes a compressible coil spring 155 (or alternatively a fuzz button) used with a rigid conductive tip insert 156. The compressible contact and the tip insert are retained by a hat 157 attached to the feedthrough pin by crimping, snap-on feature, biocompatible adhesive, or a combination thereof. For a snap-on attachment, the hat may have at least one dimple 158 that retains the hat against undercut in the corresponding area of a feedthrough pin 159. The rigid conductive insert provides a robust contact tip for connecting to the lead's tubular contact. The compressible contact can be preloaded (pre-compressed) by hat 157.

Figure 21:
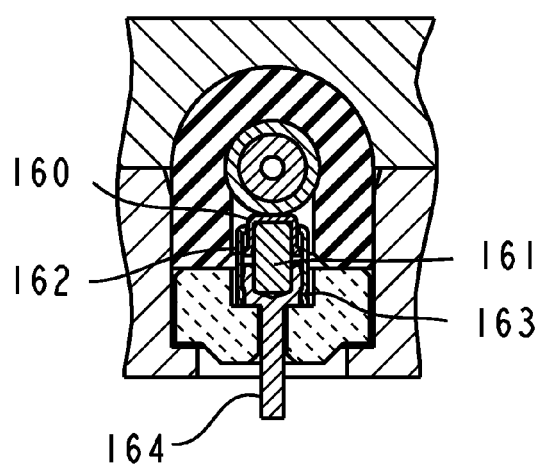
FIG. 21 is a variation of cross-sectional view of FIG. 13, taken as indicated by the lines 13-13 of FIG. 12, where the compressible contact is a conductive button or a coil spring, secured and preloaded by a cylindrical hat attached to the feedthrough pin.

FIG. 21 is a variation of the connector shown in FIG. 20 where a larger diameter compressible contact can be accommodated. A rigid (non-resilient) conductive tip insert 160 is a drawn or machined part that partially encloses and protects the compressible contact 161. The compressible contact and the rigid contact tip are further protected and retained by hat 162 attached to the feedthrough pin using a snap-on feature and/or adhesive. For a snap-on attachment, hat 162 may have at least one dimple 163 that retains the hat against an undercut in the corresponding area of a feedthrough pin 164. The compressible contact can be preloaded (pre-compressed) by hat 162

Figure 22:
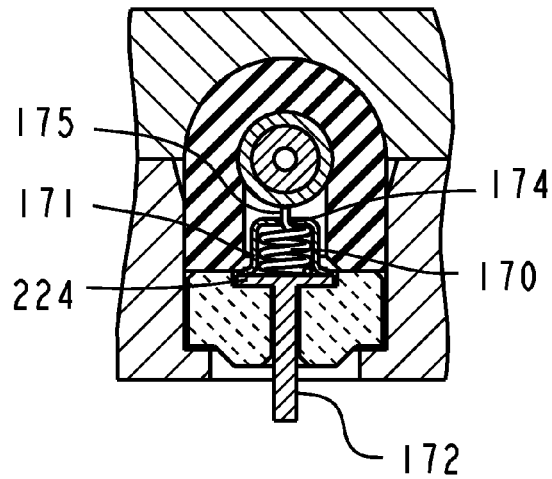
FIG. 22 is a variation of cross-sectional view of FIG. 21, taken as indicated by the lines 13-13 of FIG. 12, where the compressible contact is a coil spring, protectively confined in a hat welded to the feedthrough pin.

FIG. 22 is a variation of the connector shown in the cross-sectional view of FIG. 21 where the compressible contact is a coil spring 170, which is protectively confined in a cylindrical hat 171 attached to a nail-head 172 of a feedthrough pin 173, preferably by welding. A pilot hole 174 on the top of the hat precisely positions and guides contact tip 175 on the spring's outer end, to assure mating alignment to the lead's tubular contact. The contact spring can also be pre-loaded by the hat.

Figure 23:
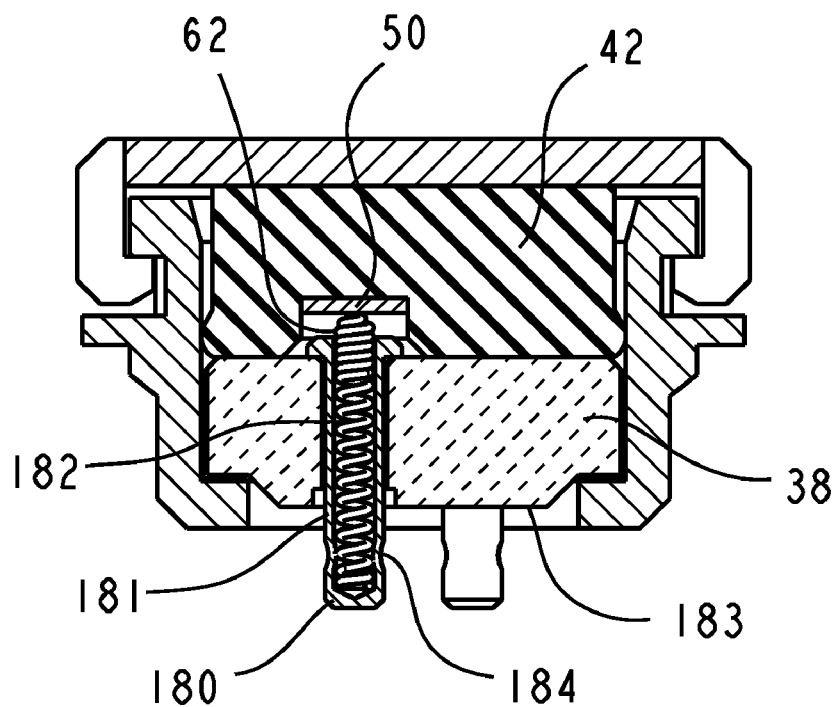
FIG. 23 is a variation of the cross-sectional view of FIG. 3, taken as indicated by the lines 2-2 of FIG. 1, where the tubular section of the feedthrough pin and the compressible contact extend beyond the bottom side of the dielectric substrate and are crimped together from the feedthrough interior side.

FIG. 23 is a partial cross-sectional view of a variation of the connector shown in the cross-sectional view of FIG. 3 with an alternate compressible contact embodiment. A tubular section 181 of a feedthrough pin 180 and a compressible contact 182 extend beyond the interior side 183 of dielectric substrate 38 (the side that is in the interior of the device case after feedthrough is attached to the device's case). The tubular section can be crimped as shown at 184 to retain the compressible contact in the tubular section and to enhance electrical connection between the compressible contact and the feedthrough pin. This contact embodiment also demonstrates how a long, high-compliance compressible contact can be employed without increasing connector height.

Figure 24:
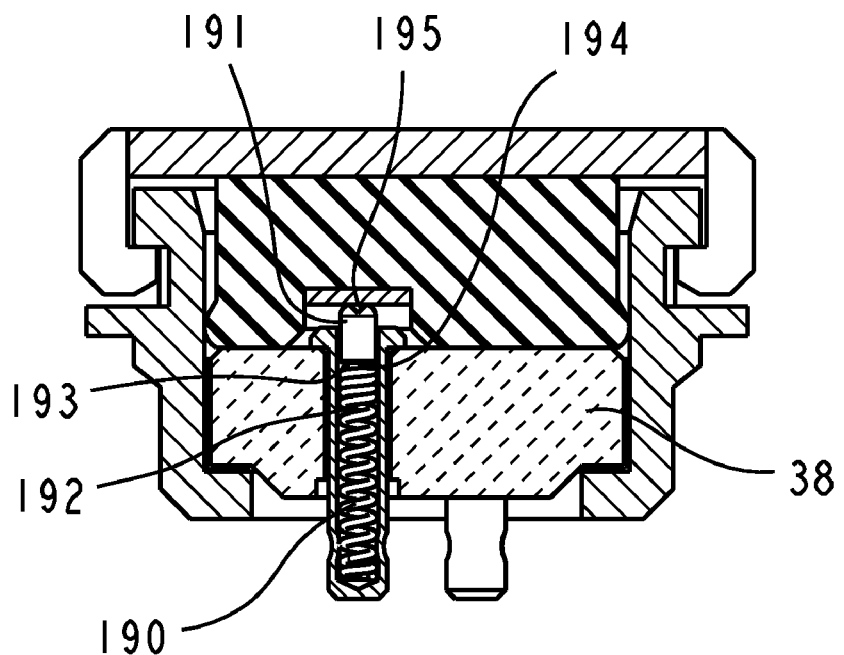
FIG. 24 is a variation of the connector of FIG. 23 where the compressible contact has a rigid contact tip provided by a conductive contact insert attached to the outer end of the coil spring.

FIG. 24 is a variation of the connector shown in FIG. 23 where a compressible contact 190 has a rigid conductive tip insert 191, attached to the outer end of the coil spring. The tip insert is a stepped diameter round pin, with a larger diameter tip 191 and a smaller diameter shank 192 (obscured by the spring coils). The tip diameter is sized for a free movement within the tubular opening of the feedthrough pin, and it generally matches the outside diameter of the coil spring. The smaller diameter shank is sized for a snug fit inside the coil spring where it is inserted until a pin shoulder 193 rests on the outer end of the coil spring. The pin can be retained in the spring by an interference fit and/or attached to it, preferably by welding, as shown at 194 or just below.

The contact tip can further have at least one cut, such as a V-shaped slot 195, to provide pointed contact point features. Such features help in self-cleaning of the contact during mating and thus help to assure a low contact interface resistance at moderate contact loads.

Advantages

From the description above, a number of advantages of various embodiments of the disclosed connector become evident:

(A) A feedthrough-based header is easier to manufacture than a molded header since it does not require fan-out wiring from feedthrough pins to contacts in the header. In contrast to the molded header, which requires sealing of the fan-out connections and forming a lead receiving cavity using molding processes, the feedthrough-based connector requires only addition of compressible contacts, to a pre-fabricated, pre-tested feedthrough.

(B) Smaller radial or transverse (x-y) contact dimensions (i.e., dimensions normal to the contact longitudinal or z-direction axis) are possible as the contact spring length is increased. Advantageously, the compressible contact can be coaxially confined in a tubular section of the feedthrough pin so that even substantial contact length does not significantly impact connector overall height.

(C) The small radial dimensions of the compressible contacts and the low effective contact height (contact tip extension into exterior feedthrough cavity) relatively independent of the contact length, enable low profile connectors with closely spaced contacts. A large number of connections can thus be provided in a small connector volume.

(D) A small connector size is achieved without compromising compressible contact performance. The high-aspect-ratio compressible contacts have a high axial (z-direction) compliance and desirable contact parameters (high deflection capability at a moderate spring rate) relative to their small radial size, which makes the contact forces less sensitive to the worst case assembly conditions and repeated mating.

(E) The compressible contacts are protected from inadvertent handling damage by being confined in a tubular body of the feedthrough pin or in a protective structure attached to the feedthrough pin. A hard contact tip can be added on top of the compressible contact to enhance contact point robustness and/or to provide contact preload for more consistent contact force.

(F) In the first embodiment of the connector for iso-diametric leads (FIG. 8), an Ω-profiled seal and a complimentarily profiled cover channel are used to safely insert the lead into the cover and to positively retain it through connector pressurization. Also advantageously, the easily achievable dimensions of this connector embodiment are a depth of approximately 5.0 mm, a length of approximately 10.5 mm, and a breadth of approximately 9.5 mm. The resulting connector volume is approximately 0.5 cc, which is less than 40% of the volume required for a comparable two-lead connector discussed in the Prior Art section above.

(G) Numerous small-sized clamping options are enabled when the metal feedthrough housing is used as the sustaining structure for connector pressurization. Small and robust engagement or retention features are possible in a metal feedthrough housing that would be impractical in a molded header. The third embodiment for iso-diametric leads demonstrates efficient use of retaining clips. The easily achievable width of this two-lead connector embodiment is 7.0 mm, which makes it suitable for a placement on an edge periphery of a small-dimensioned device. In contrast, the width of an equivalent two-lead prior art connector cited above is 13 mm. Such a drastic reduction of connector size is enabled by the use of low profile compressible contacts with small radial dimensions in combination with a space efficient retention means.

Further advantages will be evident to those skilled in the art.

RAMIFICATIONS AND SCOPE

While the connector has been described by means of specific embodiments, numerous modifications and variations known to those skilled in the art or disclosed may be employed without departing from the scope of the invention set forth in the claims. For example, the materials, dimensions, shapes, and sizes of all parts may be adapted to a particular need. The number of contacts in particular can vary greatly (up to 24 or more) thus significantly affecting envelope dimensions of a connector assembly. The feedthrough housing may be of two-piece construction, the two pieces joined by welding or another method. The exterior side of the feedthrough housing can be made of a polymer, added after feedthrough brazing operation. The lead terminal cross-sectional profile and the matching lead receiving lumen may be non-circular. The lead proximal terminal may have rectangular or oval cross-sectional profile with terminal contacts profiled accordingly. The flat terminal may have round outline rather than paddle-shaped, with a polar rather than linear contact pad pattern. An integral seal system can be replaced with separate seal components and vice versa. Additional seal components may be added if desirable. The dielectric substrate can be a multi-layer substrate or even a two-piece construction wherein the inner piece provides a hermetic seal and the outer seal provides structural support and accommodates the compressible contacts. Additional components, such as a filter capacitor or a printed circuit board can be added to the interior side of the dielectric substrate. The compressible contacts may be installed directly into metalized holes in a dielectric substrate. As to every element, it may be replaced by one of multiple equivalent alternatives, only some of which are disclosed in the specification.

Thus the scope should be determined, not by the examples or specifics given, but by the appended claims and their legal equivalents.

I claim:

1. An implantable electrical connector assembly for separably connecting at least one multi-conductor implantable lead to an implantable device having electronic circuitry contained inside a hermetically sealed case, comprising:
   (a) a hermetic electrical feedthrough attached to the device case, the feedthrough comprising a feedthrough housing having inside walls, at least one dielectric substrate having an exterior side and an interior side, and a plurality of conductive feedthrough pins; the hermetic feedthrough having at least one exterior cavity formed by the inside walls of the feedthrough housing and the exterior side of the dielectric substrate; the feedthrough pins providing pass-through connections from the exterior cavity to the electronic circuitry in the implantable device, each feedthrough pin having a tubular section adapted to protectively confine and electrically interface a compressible contact;
   (b) at least one implantable lead with proximal contact terminal comprising a plurality of lead contacts, each lead contact connected to at least one conductor of the multi-conductor lead, the lead contacts disposed in a pattern directly mapped to the plurality of the feedthrough pins;
   (c) a plurality of resilient compressible contacts, each compressible contact electrically connected to a respective feedthrough pin and protectively confined and retained in a tubular section thereof, so that only an outer tip of each contact projects from the tubular section, the tip adapted to making a separable electrical connection to the corresponding lead contact when the connector is pressurized;
   (d) at least one elastomeric seal having at least one lumen for receiving the lead proximal terminal without significant interference, the seal having a substantially flat bottom side cooperating with the feedthrough exterior cavity, and a profiled top side cooperating with a clamping cover, the bottom side having apertures so that, after the lead terminal is inserted into the lumen to form a lead-seal assembly, each lead contact is exposed from the bottom side of the seal and can be accessed by the corresponding compressible contact integrated with the feedthrough pin, the seal further providing an electrical isolation of the non-common contacts when compressed against the exterior side of the dielectric substrate; and
   (e) a clamping means, adapted to detachably engage the feedthrough housing, comprising at least one clamping cover and at least one fastener, the cover having at least one channel with a profile generally matching the profiled top side of the seal, wherein when the cover is clamped to the feedthrough housing, the connector is pressurized by forcing the lead contacts against the compressible contacts and the seals are activated by compressing the elastomeric seal between the cover and the exterior side of the dielectric substrate.

2. The connector assembly of claim 1 wherein the seal cross-sectional profile is Ω-shaped and the clamping cover channel has a complimentary Ω-shaped profile adapted to receive the lead-seal assembly with slight interference, so that after the lead-seal assembly is inserted into the cover channel, the lead-seal assembly is prevented from being radially dislodged from the cover channel.

3. The connector assembly of claim 1 wherein the elastomeric seal has two lead-receiving lumens side-by-side and the lead-seal assembly comprising two leads is adapted to be accommodated in a single feedthrough exterior cavity.

4. The connector assembly of claim 1 wherein the lead-seal assembly is inserted into the feedthrough cavity with slight interference so as to be securely retained therein prior to connector pressurization.

5. The connector assembly of claim 1 wherein the clamping cover is secured to the feedthrough housing with two U-shaped clips having latches on their ends, the latches adapted to engage undercuts on the feedthrough housing, the undercuts extending through the feedthrough middle section to allow engagement of a temporary clamping tool to aid in clip installation and removal, and the cover further having reliefs adjacent to the clips to provide tool access for clip disengagement.

6. The connector assembly of claim 1, further including a screw for securing the clamping cover to the feedthrough housing.

7. The connector assembly of claim 1 further including a C-profiled retaining sleeve, adapted to receive the lead-seal assembly by interference fit, so that when the lead-seal assembly is pressed into the retaining sleeve, the radial pressure on the seal causes the seal between adjacent lead contacts to be activated prior to connector pressurization.

8. The connector assembly of claim 1 wherein the feedthrough pins have tubular sections open to the exterior feedthrough cavity, at least a portion of each tubular section and the corresponding portion of the compressible contact contained between the exterior and interior sides of the ceramic substrate.

9. The connector assembly of claim 8 wherein the tubular sections of the feedthrough pins and the compressible contacts contained therein reside substantially within the thickness of the dielectric substrate, between the exterior and interior sides of the dielectric substrate.

10. An implantable electrical connector assembly for separably connecting at least one multi-conductor implantable lead to an implantable device having electronic circuitry contained inside a hermetically sealed case, comprising:
(a) a hermetic electrical feedthrough attached to the device case, the feedthrough comprising a housing having inside walls, at least one dielectric substrate having an exterior side and an interior side, and a plurality of conductive feedthrough pins; the hermetic feedthrough having at least one exterior cavity formed by the feedthrough housing inside walls and the exterior side of the dielectric substrate; the feedthrough pins providing pass-through connections from the exterior cavity to the device electronic circuitry in the interior of the implantable case, each feedthrough pin being adapted to protectively confine and electrically interface a compressible contact;
(b) at least one implantable lead with a proximal contact terminal having a plurality of lead contacts, each lead contact connected to at least one conductor of the multi-conductor lead, the lead contacts disposed in a pattern mapped directly to the plurality of the feedthrough pins;
(c) a sealing means adapted to provide electrical isolation of the non-common contacts when the connector is pressurized;
(d) a plurality of resilient compressible contacts, each compressible contact electrically connected to a respective feedthrough pin and protectively confined and retained in a tubular section of a contact assembly, so that only an outer tip of each contact projects from the tubular section, the tip adapted to making a separable electrical connection to the corresponding lead contact when the connector is pressurized; and
(e) a connector clamping means, designed to detachably engage the feedthrough housing, comprising at least one clamping cover and at least one fastener and adapted to pressurize the connector contacts and seal interfaces by forcing the lead proximal contacts against the compressible contacts and compressing the sealing means against the exterior side of the dielectric substrate.

11. The connector assembly of claim 10, further including a hat attached to the feedthrough pin so that the hat provides the tubular section adapted to protectively confine and retain the compressible contacts.

12. The connector assembly of claim 10 wherein the compressible contacts are fuzz buttons.

13. The connector assembly of claim 10 where the compressible contacts are metal-particle-filled elastomer buttons.

14. The connector assembly of claim 10 wherein each feedthrough pin has a tubular section open to the exterior feedthrough cavity, with at least a portion of the tubular section and the corresponding portion of the compressible contact contained between the exterior and interior sides of the dielectric substrate.

15. The connector assembly of claim 14 wherein the tubular sections of the feedthrough pins and the compressible contacts contained therein reside substantially within the thickness of the dielectric substrate, between the exterior and interior sides of the dielectric substrate.

16. The connector assembly of claim 14 wherein the tubular sections of the feedthrough pins and the compressible contacts therein extend beyond the interior side of the dielectric substrate and the tubular sections are crimped on the interior side of the dielectric substrate to retain the compressible contacts.

17. The connector assembly of claim 14 wherein the compressible contacts are coil springs, each coil spring having an inner end and an outer end.

18. The connector assembly of claim 17 wherein the coil spring has tightly wound coils at the outer end that form a contact tip.

19. The connector assembly of claim 17 wherein at least a part of at least one of the coils on the inner end of each coil spring has a larger outside diameter than the diameter of the corresponding portion of the tubular section so as to create an interference fit, and the compressible contacts is retained in the tubular section by the resulting interference.

20. The connector assembly of claim 10 wherein the compressible contacts further include rigid contact inserts on their outer ends.

21. The connector assembly of claim 20 wherein the rigid contact inserts are permanently attached to the outer ends of the compressible contacts by welding.

22. The connector assembly of claim 20, further including a plurality of washer-shaped inserts, permanently attached to the outer ends of the feedthrough pins and adapted to retain the compressible contacts and to preload the contacts.

23. The connector assembly of claim 20 further including a hat attached to the feedthrough pin and adapted to retain the compressible contacts and to preload the contacts.

24. An implantable electrical connector assembly for separably connecting at least one multi-conductor implantable lead to an implantable device having electronic circuitry contained inside a hermetically sealed case, comprising:
(a) a hermetic electrical feedthrough attached to the device case, the feedthrough comprising a housing having inside walls, at least one dielectric substrate having an exterior side and an interior side, and a plurality of conductive feedthrough pins hermetically sealed in the dielectric substrate; the hermetic feedthrough having at least one exterior cavity formed by the inside walls of the feedthrough housing and the exterior side of the dielectric substrate; the feedthrough pins providing pass-through connections from the exterior cavity to the electronic circuitry in the interior of the implantable device, each feedthrough pin having a tubular section open only to the exterior cavity and adapted to receive, retain, protectively confine, and electrically interface a compressible contact;
(b) at least one implantable lead with a proximal contact terminal having a paddle-shaped body with a substantially flat bottom side and a top side, the body containing a plurality of conductive contact pads, each contact pad connected to at least one conductor of the multi-conductor lead, the contact pads disposed in a pattern mapped directly to the plurality of the feedthrough pins, the contact pads exposed from the bottom side of the terminal so that each contact pad can be accessed by a corresponding compressible contact integrated with the feedthrough pin, the lead terminal body further providing a contact electrical isolation seal when compressed against the exterior side of the dielectric substrate;

(c) a plurality of resilient compressible contacts, each compressible contact having an inner end and an outer end, the compressible contact electrically connected to a respective feedthrough pin and protectively confined and retained in a tubular section thereof, so that only the outer end of the compressible contact protrudes from the tubular section, the outer end adapted to making a separable electrical connection to the corresponding contact pad when the connector is pressurized, and wherein at least a portion of the tubular section and the corresponding portion of the compressible contact are contained between the exterior and interior sides of the dielectric substrate; and (d) a connector clamping means, adapted to detachably engage the feedthrough housing, for supporting contact and seal compression loads, the clamping means arranged to exert pressure on the top side of the terminal body.

25. The connector assembly of claim 24 wherein the tubular section of the feedthrough pin and the compressible contact contained therein reside substantially within the thickness of the dielectric substrate, between the exterior and interior sides of the dielectric substrate.

26. The connector assembly of claim 24 wherein the feedthrough housing has undercuts on the outside walls, and the clamping means is a curved spring, having a first and a second end, each end having two substantially rigid side latches for slidably engaging the undercuts, so that the spring can be engaged to the feedthrough housing by slidably engaging latches on the first end, pressing the second end down until the latches on the second end align with the undercuts, and sliding the spring to centered position, whereby the spring exerts downward pressure on the top of the lead terminal body, causing the contact pads to be forcibly electrically engaged with the compressible contacts and the seal to be activated.

27. The connector assembly of claim 24 wherein the feedthrough housing has undercuts on the outside walls, and the clamping means is a clamping cover comprising a compression plate and a latching spring, the latching spring having two spring latches on each end, whereby after the latches are engaged with the undercuts of the feedthrough housing, the compression plate is supported by the spring and exerts downward pressure on the top side of the lead terminal body, causing the lead contacts to be forcibly electrically engaged with the compressible contacts and the seal to be activated.

28. The connector assembly of claim 24 wherein the lead contact pads are recessed from the bottom side of the lead terminal body so that the bottom side of the terminal body has an integral seal protruding beyond the contact pads, thereby allowing unimpeded compression of the seal when the terminal body is compressed against the exterior side of the dielectric substrate.

29. The connector assembly of claim 24 wherein the compressible contact is a coil spring having tightly wound coils on the outer end to form a contact tip.

30. The connector assembly of claim 24 wherein the compressible contact is a coil spring, wherein the outside diameter of the inner end of the coil spring is larger than the inside diameter of the corresponding portion of the tubular section, whereby the coil spring can be retained in the tubular section of the feedthrough pin by an interference fit engagement between the inner end of the coil spring and the corresponding portion of the tubular section of the feedthrough pin.

31. The connector assembly of claim 24 wherein the compressible contact further comprises a rigid conductive tip permanently attached to the outer end of the compressible contact, wherein the outside diameter of the tip is substantially equal to the outside diameter of the compressible contact.

32. The connector assembly of claim 24 wherein the tubular section of the feedthrough pin and the compressible contact therein extend beyond the interior side of the dielectric substrate and the tubular section is crimped on the interior side of the dielectric substrate to retain the compressible contact.

33. The connector assembly of claim 24 wherein the compressible contact further comprises a rigid conductive tip at the outer end and the feedthrough pin further includes an insert attached to the outer end of the feedthrough pin, the insert adapted to retain the conductive tip and the compressible contact.

* * * * *